United States Patent [19]
Pronovost et al.

[11] Patent Number: 5,786,220
[45] Date of Patent: Jul. 28, 1998

[54] ASSAYS AND DEVICES FOR DISTINGUISHING BETWEEN NORMAL AND ABNORMAL PREGNANCY

[75] Inventors: Allan D. Pronovost; Theodore T. Lee. both of San Diego, Calif.

[73] Assignee: Quidel Corporation, San Diego, Calif.

[21] Appl. No.: 431,236

[22] Filed: Apr. 28, 1995

[51] Int. Cl.⁶ .................................... G01N 33/543
[52] U.S. Cl. ................ 436/518; 435/5; 435/7.32; 435/7.92; 436/161
[58] Field of Search .................. 436/518, 7.92, 436/5, 7.32, 161

[56] References Cited

U.S. PATENT DOCUMENTS

| | | | |
|---|---|---|---|
| 4,094,963 | 6/1978 | Saxena | 424/1 |
| 4,943,522 | 7/1990 | Eisinger et al. | 435/7 |
| 4,956,302 | 9/1990 | Gordon et al. | 436/161 |
| 5,026,653 | 6/1991 | Lee et al. | 436/518 |
| 5,356,785 | 10/1994 | McMahon et al. | 435/7.92 |
| 5,399,486 | 3/1995 | Cathey et al. | 435/7.9 |
| 5,415,994 | 5/1995 | Imrich et al. | 435/5 |
| 5,424,193 | 6/1995 | Pronovost et al. | 435/7.32 |

OTHER PUBLICATIONS

B. L. Lasley et al. "Urinary hormone levels at the time of ovulation and implantation," (1985) Fertility and Sterility vol. 43, No. 6, pp. 861–867.

C. Pike–Matthews et al. "Serum Progesterone Levels as an Aid in the Diagnosis of Ectopic Pregnancy," (1986) Obstetrics & Gynecology vol. 68, No. 3, pp. 390–394.

T. R. Yeko et al. "Timely diagnosis of early ectopic pregnancy using a single blood progesterone measurement," (1987) Fertility and Sterility vol. 48, No. 6, pp. 1048–1050.

R. H. Buck et al. "Serum progesterone in the diagnosis of ectopic pregnancy: a valuable diagnostic test?," (1988) Fertility and Sterility vol. 50, No. 5, pp. 752–755.

M. V. Sauer et al. "Rapid measurement of urinary pregnanediol glucuronide to diagnose ectopic pregnancy, " (1988) Am J. Obstet Gynecol vol. 159, No. 6, pp. 1531–1535.

M. S. Gelder et al. "Use of a single random serum progesterone value as a diagnostic aid for ectopic pregnancy, " (1991) Fertility and Sterility vol. 55, No. 3, pp. 497–500.

T. G. Stovall et al. "Serum progesterone and uterine curettage in differential diagnosis of ectopic pregnancy, " (1992) Fertility and Sterility vol. 57, No. 2, pp. 456–458.

R. P. Buyalos et al. "Serum β–Human Chorionic Gonadotropin, Estradiol and Progesterone as Early Predictors of Pathologic Pregnancy," (1992) Journal of Reproductive Medicine vol. 37, No. 3, pp. 261–266.

D. S. Cunningham et al. "Suboptimal Progesterone Production in Pathologic Pregnancies," (1993) Journal of Reproductive Medicine vol. 38, No. 4, pp. 301–305.

(List continued on next page.)

*Primary Examiner*—James C. Housel
*Assistant Examiner*—Ginny Allen Portner
*Attorney, Agent, or Firm*—Townsend and Townsend and Crew LLP

[57] ABSTRACT

Methods and devices for distinguishing between normal and abnormal pregnancies are provided. The methods rely on determining the concentration of progesterone or progesterone metabolite in a patient sample, where a concentration above a threshold value is indicative of a normal pregnancy. Preferably, the concentration of hCG is determined simultaneously, where an hCG concentration above a threshold value provides confirmation that the individual being tested is pregnant. An exemplary test device comprises a lateral flow membrane having zones for capturing label in response to the progesterone and hCG concentrations, respectively. Visible label is accumulated when the hCG concentration exceeds the threshold value but is absent when the progesterone concentration exceeds the threshold value.

19 Claims, 3 Drawing Sheets

OTHER PUBLICATIONS

C. M. Grosskinsky et al. "hCG,. Progesterone, Alpha-Fetoprotein, an Estradiol in th Identification of Ectopic Pregnancy."(1993) Obstetrics & Gynecology vol. 81, No. 3, Part 1, pp. 705–709.

T. G. Stovall et al. "Ectopic Pregnancy Diagnostic and Therapeutic Algorithms Minimizing Surgical Intervention." Journal of Reproductive Medicine vol. 38, No. 10, pp. 807–812.

J. J. Stern et al. "Early diagnosis of ectopic pregnancy using receiver–operator characteristic curves of serum progesterone concentrations," (1993) Human Reproduction vol. 8, No. 5, pp. 775–779.

Leusden, H A van, Vitam Horm, 1972, vol. 30, pp. 281–361, "Hormonal Changes in Pathological Pregnancy".

Jouppila, P et al, Obstet Gynecol, 1980 Jan., vol. 55 No. 1, pp. 42–77.

Dawood, M. Y., Am J Obstet Gynecol, 1975 Dec. 1, vol. 123, No. 7, pp. 762–765.

Goebel, R. Horm Res., 1978, vol. 9, No. 6, pp. 336–364.

Isaacs, J et al, Fertility and Sterility, vol. 62, No. 3, Sep. 1994, pp. 452–455.

Kuscu, E et al, Materia Medica Polona, vol. 25, No. 2–4, 1993, pp. 149–152, "The hormonal profile in ectopic pregnancies".

Deutchman, M, Am Fam Physician, 1991, Nov., vol. 44 (5 suppl) 15S–30S, ref 45.

Hahlin, M et al, Hum Reprod (OXF) vol. 5 No. 5, 1990, pp.622–626.

Azuma, K et al, j Clin Endocrinolo Metab, Jul. 1993, vol. 77 No. 1, pp. 195–198.

Yuen, B H et al, Obstet Gynecol vol. 57, No. 2,1981, pp. 07–214.

Hibbard, BM, Br. Med J, 1971 Mar. 13, 1(749), pp. 593–595.

Zourlas, P.A., Clin Exp Obstet Gynecol, 1992, vol. 19 No. 3, pp.180–188.

Lenten , E. A. et al, Fertil Steril, Jun. 1982, vol. 37 No. 6, pp. 773–778.

ASSAYS AND DEVICES FOR DISTINGUISHING BETWEEN NORMAL AND ABNORMAL PREGNANCY

BACKGROUND OF THE INVENTION

1. Field of the Invention

The present invention relates generally to met hods and devices for distinguishing between normal and abnormal pregnancies in pregnant human females. More particular y, the present invention relates to methods and devices for determining progesterone or progesterone metabolite concentrations optionally in combination with human chorionic gonadotropin concentrations and relating said concentration (s) to pregnancy status.

Pregnancy in human females can be terminated by unfortunate circumstances, including spontaneous abortion and ectopic pregnancy. While the latter event cannot be treated to preserve the pregnancy, spontaneous abortion can be avoided in many cases by taking proper corrective actions. In booth cases, and in all other types of abnormal pregnancies, it is desirable to determine the abnormal status of the pregnancy at as early a date as possible.

Much research has been done to show the relationship between progesterone levels and ectopic pregnancy or spontaneous abortion. Generally, it has been found that drops in serum progesterone levels correlate in a predictable manner with both ectopic pregnancy and spontaneous abortion. Progesterone metabolite levels in urine also correlate with both ectopic pregnancy and spontaneous abortion, but are generally less well studied. Elevated or continually doubling serum human chorionic gonadotropin (hCG) levels are also known to correlate with normal pregnancy.

Despite the available knowledge with regard to progesterone and hCG levels in pregnant females, rapid screening tests for confirming the normal status of the pregnancy are not generally available. In particular, it would be desirable to provide rapid screening assays which could be utilized in blood, plasma, serum or urine samples from the pregnant female to confirm the continuing normal status of the pregnancy. Such tests should be rapid, preferably taking no more than several minutes to run, and should be convenient so that the tests could be performed at home by the female or at institutions by individuals with little or no specific training in diagnostics. It would be particularly desirable if such tests would rely on both progesterone (or progesterone metabolite) levels and hCG levels in order to confirm the normal status of the pregnancy. It would be further desirable if the tests provided two separate signals, wherein the presence of one signal and the absence of another signal was indicative of a normal pregnancy.

2. Description of the Background Art

The monitoring of multiple serum hormone levels, including progesterone and hCG, for the prediction of ectopic pregnancy is described in Stovall and Ling (1993) J. Rep rod. Med. 38:807–812; Grosskinsky et al. (1993) Obstet. Gynecol. 81:705–709; and Buyalos et al. (1992) J. Reprod. Med. 37:261–265. The monitoring of serum progesterone levels for the prediction of ectopic pregnancy is described in Stern et al. (1993) Hum. Reprod. 8:775–779; Dean et al. (1993) J. Reprod. Med. 38:301–305; Stovall et al. (1992) Fert. Steril. 57:456–458; Gelder et al. (1991) Fert. Steril. 55:497–500; Buck et al. (1988) 50:752–755; Yeko et al. (1987) 48:1048–1050; and Mathews et al. (1986) Obstet. Gynecol. 68:390–394. The monitoring of urinary progesterone metabolite as a diagnostic marker for ectopic pregnancy is described in Sauer et al. (1988) Am. J. Obstet. Gynecol. 159:1531–1535. The monitoring of urinary estrone, progesterone, and hCG levels of women undergoing artificial insemination was described in Lasley et al. (1985) Fert. Steril. 43:861–867.

SUMMARY OF THE INVENTION

The present invention provides methods and deices for the rapid testing of patient samples from pregnant human females to confirm normal pregnancy status. Usually, when the tests show normal status, no further testing of the individual is warranted. When the test shows abnormal status, however, further testing should be performed to determine the cause of the abnormalcy, including whether the pregnancy is ectopic or the patient is at risk of spontaneous abortion. Such further testing can include ultrasound examination, detailed and quantitative determinations of pregnancy hormones over time to determine changes in levels, and the like. The tests of the present invention are particularly useful in testing over the first six months of pregnancy, preferably during the period from four weeks to three months after conception.

Methods for distinguishing between normal and abnormal pregnancy according to the present invention comprise obtaining a sample from the female. The concentration of progesterone or progesterone metabolite is then determined in the patient sample. When a progesterone concentration above a threshold value in the range from 5 ng/ml to 50 ng/ml is found in a blood, plasma or serum sample, or a corresponding progesterone metabolite concentration is found in urine, the pregnancy appears to be normal. Usually, the progesterone metabolite is progesterone-3α-glucuronide (PDG), and the threshold concentration in urine is in the range of from 5 µg/ml to 50 µg/ml.

Preferably, the methods of the present invention will further comprise determining the concentration of human chorionic gonadotropin (hCG) in the same specimen or sample in which the progesterone or progesterone metabolite was determined. A hCG concentration above a threshold value typically in the range from 25 mIU/ml to 50 mIU/ml, provides confirmation that the tested individual is pregnant at the time of testing. The progesterone concentration is of diagnostic value only if the patient is pregnant at the time of testing. That is, a progesterone concentration below the threshold value (as defined above) is normal for non-pregnant human females when hCG levels are less than 25 mIU/ml and are not rising. Inclusion of a simultaneous hCG determination in the assay protocol and device thus helps to rule out false predictions of abnormal pregnancy when in fact the individual was not pregnant at the time of testing.

In a particularly preferred aspect of the present invention, the tests will be performed on a single test matrix where the presence or absence of signal on the test matrix is indicative of the normal status of the progesterone and/or hCG level. In a most preferred aspect of the present invention, the presence of a normal amount of one of the two target hormones will produce a signal on the matrix while the presence of a normal amount of the other target hormone will prevent production of a signal. In this way, failure in either the test device or test procedure which results in the complete absence of signal will be flagged since the test should always result in at least one signal, i.e., the hCG line or actual result, being produced (assuming that the female is pregnant).

Methods and devices of the present invention are useful for assisting in distinguishing between normal and abnormal pregnancies. That is, the test results will not be definitive of the status of the pregnancy. While positive test results can normally be relied on for indicating a normal pregnancy, negative test results will usually require further testing to confirm that the pregnancy is in fact abnormal and to determine the particular cause of the abnormalcy.

A preferred method according to the present invention comprises applying a specimen to a flow matrix, where the specimen is blood, plasma, serum, or urine. A visually observable label, usually in the form of a colored particle, is selectively bound within a first binding region on the flow matrix whenever the concentration of progesterone or progesterone metabolite falls below the threshold value. Thus, signal will be produced when the progesterone or progesterone metabolite level indicates that the pregnancy is abnormal.

A visually observable label will also be selectively bound within a second binding region on the flow matrix when the hCG concentration in the sample exceeds the threshold value. Thus, the label will be bound within the second binding region only when the female is pregnant. Test results which show signal in the second binding region but absent from the first binding region will thus be consistent with a normal pregnancy. Optionally, the color produced in the first binding region can be different than that produced in the second binding region to facilitate reading the results. For example, the first binding region color can be blue (as a control) while the second binding region can be red (to indicate a problem).

The test device according to the present invention comprises a matrix for receiving a patient sample. Reagents are provided on the matrix for indicating when a progesterone or progesterone metabolite concentration in the sample applied to the matrix exceeds the threshold value. Reagents within a separate region of the matrix are provided which indicate when the hCG concentration in the applied sample exceeds the threshold value. In a preferred test device, the matrix further defines a flow path. A sample-receiving zone is located at an upstream end of the flow path. A first labelling zone is provided on the flow path downstream from the sample-receiving zone, where the first labelling zone comprises a progesterone or progesterone-binding substance attached to a visually observable label. A first capture zone is disposed on the flow path downstream from the first labelling zone. The first capture zone comprises progesterone, progesterone metabolite, or an analog of progesterone or progesterone metabolite which will bind to visually observable particles having progesterone-binding substance or progesterone metabolite-binding substance bound thereto. Alternatively, the first capture zone may comprise progesterone-binding substance or progesterone metabolite-binding substance which will capture labelled progesterone, labelled progesterone metabolite or analog, in inverse proportion to the amount of native progesterone present in the sample. In either way, label is bound within the first capture zone only if progesterone or progesterone metabolite in the sample falls below a threshold value.

A second labelling zone is also disposed on the flow path downstream from the sample-receiving zone. The second labelling zone provides for attaching a visual label to hCG in the sample flowing through the labelling zone. A second capture zone is disposed on the flow path downstream from the second labelling zone and spaced-apart from the first capture zone. The second capture zone provides for capturing visual label which has been bound to hCG within the labelling zone. Such binding is indicative of a threshold hCG concentration consistent with normal pregnancy. Any of the progesterone detection protocols described above could be adopted for the analogous detection of hCG.

As a second alternative, the test matrix may comprise a first displacement zone between the first labelling zone and the first capture zone. The first displacement zone will comprise excess bound progesterone, progesterone metabolite or an analog of progesterone or progesterone metabolite, when the first label zone contains labelled progesterone binding substance. In this way, the presence of native progesterone in the sample will prevent capture of the labelled binding substance within the first displacement zone (where it is not observed) and will permit further migration of the label to the first capture zone, where it is captured and observed. The first displacement zone will comprise excess anti-progesterone binding substance when the first labelling zone contains labelled progesterone, progesterone metabolite, or analog of progesterone or progesterone metabolite. In this way, the presence of native progesterone in the sample will prevent capture of the labelled binding substance within the first displacement zone (where it is not observed) and will permit further migration of the label to the first capture zone, where it is captured and observed.

DESCRIPTION OF THE SPECIFIC EMBODIMENTS

Figure 1:
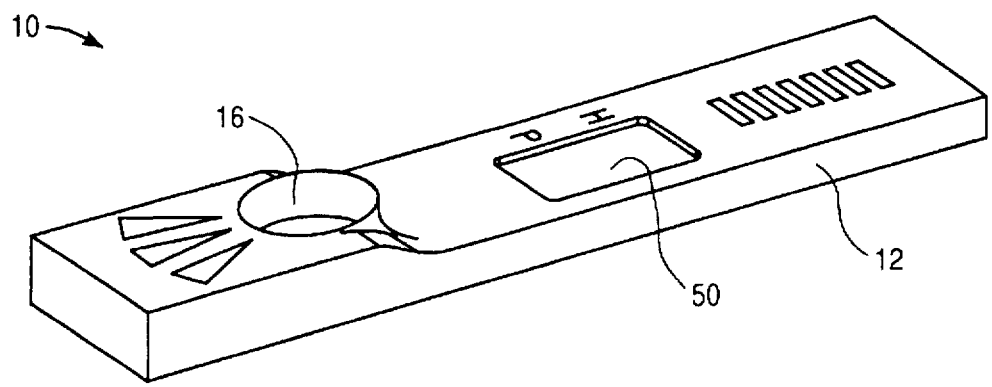
FIG. 1 is a perspective view of a test device constructed in accordance with the principles of the present invention.
Figure 2:
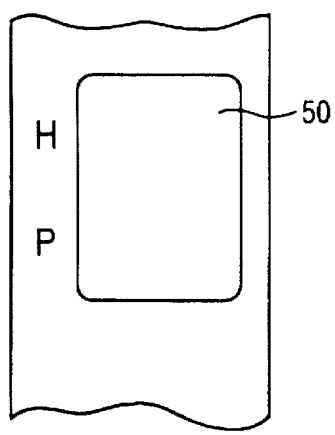
FIG. 2 is a detailed view of the label capture zone of the device of FIG. 1, shown without label bound therein.

The present invention provides methods and devices for confirming the normal status of pregnancy in a pregnant human female. Generally, the methods and devices rely on detecting the concentration of progesterone or progesterone metabolite in a patient sample or specimen, where the concentration is correlated with pregnancy status. In particular, a progesterone concentration above a threshold value in the range from 5 ng/ml to 50 ng/ml in blood, plasma, or serum, is indicative of a normal pregnancy. Similarly, the corresponding progesterone metabolite concentration in urine is also indicative of a normal pregnancy. Usually, the progesterone metabolite measured in urine will be pregnanediol-3α-glucuronide (PDG), where a value in excess of a threshold concentration in a range from 5 µg/ml to 50 µg/ml is indicative of a normal pregnancy. Other metabolites which may be measured include pregnanedione, pregnanetriol, and 17-hydroxy progesterone.

The methods and devices of the present invention will usually provide for detection of human chorionic gonadotropin (hCG) concentrations in addition to the progesterone or progesterone metabolite concentrations. Elevated hCG levels are a common marker of pregnancy, with suitable threshold values for measurement being in the range from 25 mIU/ml to 100 mIU/ml. Usually, patient hCG levels remain elevated above such threshold values even when the pregnancy is abnormal, including both ectopic pregnancies and pregnancies at risk of spontaneous abortion. Thus, the hCG determination in the present invention is performed as an indication that the female being tested is in fact pregnant. However, testing for hCG simultaneously with the progesterone/progesterone metabolite testing also acts as a control to confirm the test is being performed properly and that the test materials remain active. That is, test results which are negative for both hCG and progesterone are likely to mean that the patient was either not pregnant to begin with, that an error has been made in the testing protocol, or that the test materials have been compromised in some manner.

In a particularly preferred aspect of the present invention, the test methods and devices will provide a visually observable signal when the hCG level in the sample being tested is above the threshold concentration value. Conversely, a visually detectable signal will be provided when the progesterone or progesterone metabolite level is below the threshold value which is characteristic of a normal pregnancy. Thus, pregnant females experiencing a normal pregnancy will be expected to produce a test result having a visual signal correlated with hCG concentration and no visual signal related to progesterone or progesterone metabolite concentration. If the patient is experiencing an abnormal pregnancy, or the test protocol or test materials have been inadequate in some manner, the result will be positive or negative for both hormones being tested.

Test devices suitable for performing assays according to the present invention will comprise a matrix having a first reagent system capable of detecting the presence of progesterone and/or a progesterone metabolite in a patient sample applied to the matrix. Preferably, the matrix will also include a second reagent system for detecting the presence of hCG in the patient sample. The matrix may be any conventional solid phase of a type generally used in performing immunoassays, including dipsticks, membranes, absorptive pads, beads, microtiter wells, test tubes, and the like. Preferred are test devices which may be conveniently used by the patient for self-testing or by other testing personnel having minimal or no previous training. Such preferred test devices include dipsticks, as described in European Patent 125 118 B1; membrane assay systems as described in U.S. Pat. Nos. 4,632,901; 4,818,677; and 5,079,170; and lateral flow assay systems as describes in U.S. Pat. Nos. 4,861,711 and 4,943,522; European Patent Applications 306 772 and 276 152; and British Patent Application 2,204,398. The preparation and use of such conventional test systems is well described in the patent and medical literature.

For all such test devices and matrices, reagent systems will preferably be provided to permit the simultaneous detection of both progesterone and/or progesterone metabolite and hCG in response to contacting the matrix with a single patient sample (with or without sample dilution as needed). The presence of a threshold concentration or amount of each target hormone in the patient sample will be indicated by the presence or absence of a visual signal produced on the matrix by the reagent system. The reagent systems may provide for direct (non-competitive) binding of a visual label onto a reaction zone on the matrix in response to the presence of the target hormone in the sample. Alternatively, the reagent system may provide for noncompetitive binding of a visual label onto the reaction zone, where presence of the target hormone in the sample inhibits binding of the visual label. In a preferred aspect of the present invention, the reagent systems will provide for direct (non-competitive) binding of label within the reaction zone associated with hCG and noncompetitive binding of label within the reaction zone associated with progesterone and/or progesterone metabolite. In this way, normal pregnancy will be indicated by the presence of visual label within the hCG reaction zone and the absence of visual signal within the progesterone/progesterone metabolite reaction zone. The complete absence of visual label from the test device will thus mean either that the patient was not pregnant to being with or that the test has been run improperly. The presence of label only within the hCG reaction zone indicates that the test was most likely performed properly and that the patient appears to be experiencing a normal pregnancy. Only when visual label is present in both reaction zones is the patient alerted that further testing is warranted.

Preferred lateral flow assay devices according to the present invention comprise a matrix defining a flow path, a sample receiving zone for receiving the fluid sample onto the matrix, a labelling region downstream from the sample receiving zone for introducing label into sample flowing through the region in a manner which is mediated by the presence of target hormone within the sample, a capture region which captures label in a manner which is also mediated by the presence of target hormone in the sample, and an absorptive zone for receiving the sample after is has passed through all upstream zones and regions. In the exemplary assay device, the labelling region includes a first labelling zone comprising a progesterone- or progesterone metabolite-binding substance attached to a visually observable particle, wherein progesterone or progesterone metabolite present in sample flowing through the second labelling zone will bind to the observable particle. Alternatively, a first displacement zone containing excess bound progesterone, progesterone metabolite, or analog thereof can be provided, in which case native progesterone above the threshold level will permit the flow of labelled antibody past the displacement zone and to the capture zone. A second labelling zone (which may physically overlap with the first labelling zone) comprises a hCG-binding substance bound to a visually observable particle, wherein hCG present in sample flowing through the zone will bind to the observable particle. It will be appreciated that the first and second labelling zones within the labelling region may be spaced-apart or coincident, where a coincident structure could be prepared by applying a mixture of the hCG-binding substance and the progesterone or progesterone metabolite to the matrix over a single area. For convenience, the zones will be illustrated as being spaced-apart in connection with the drawings, but there is no reason why such physical separation is necessary.

The capture region of the lateral flow assay device will include both a first capture zone and a second capture zone. The first capture zone preferably comprises progesterone, a progesterone metabolite, or an analog of progesterone or a progesterone metabolite which will compete with native progesterone or progesterone metabolite in the sample for binding to the visual label. Thus, presence of progesterone or progesterone metabolite in the sample which exceeds a threshold value as defined above will result in absence of visual signal in the first capture zone.

The second capture zone will comprise an hCG binding substance so that visually observable particles which have bound to hCG in the labelling zone will be captured within the second capture zone. Thus, visual label within the second capture zone will accumulate and be visually observable when the concentration of hCG in the sample exceeds a threshold value as set forth above. It will be appreciated, of course, that the second capture zone could also be configured so that presence of hCG in the sample would result in absence of signal, although such a configuration is generally less preferred.

The second capture zone within the capture region will be spaced-apart from the first capture zone. Typically, the first and second capture zones will be axially spaced apart, i.e., in the direction of the flow path. It would also be possible, however, to have the capture zones transversely or otherwise spaced apart. It is necessary only that the user be able to distinguish between label which is accumulating in each of the capture zones.

The matrix of the lateral flow test devices typically provide non-bibulous lateral flow for sample applied within the receiving zone. By "non-bibulous lateral flow", it is meant liquid flow in which all of the dissolved or dispersed components of the liquid are carried at substantially equal rates and with relatively unimpaired flow laterally through or across the matrix, as opposed to preferential retention of one or more components as would occur, e.g., in materials capable of adsorbing or imbibing one or more components. A representative non-bibulous matrix material is high density polyethylene sheet material.

Bibulous materials, such as untreated paper, nitrocellulose, derivatized nylon, cellulose and the like may also be used following processing to provide non-bibulous flow. Bibulous materials may also act as filtering mechanisms as described above. Alternatively, blocking agents may block the forces which account for the bibulous nature of bibulous membranes. Suitable blocking agents include whole or derivatized bovine serum albumin or albumin from other animals, whole animal serum, casein, and non-fat dry milk.

The matrix defines a flow path for fluids applied to the matrix. The flow path is the natural movement of fluids placed on the matrix. The matrix generally has a single sample receiving zone, but could include several sample receiving zones. The sample receiving zone is a portion of the matrix to which the individual sample is applied. The sample receiving zone may remove erythrocytes, leukocytes, and/or different hormones from the sample. Generally, removal may be accomplished by immobilized antibody to the cells or hormones to be removed. The sample receiving zone may also be constructed so as to act as a filter for cellular components in a sample. The sample receiving zone may also comprise free progesterone binding substance and/or hCG binding substance in order to remove excess analyte in order to adjust the threshold level of either analyte detected, as described in copending application 07/843,681, the full disclosure of which is incorporated herein by reference, and which has been published as WO 93/17338.

A means for labelling the target hormone is present in the labelling zone. A variety of labelling complexes may be employed in the devices. The labelling means contain labelling complexes that specifically bind to the respective target hormones in the sample. The labeling complexes are often a first target hormone binding substance bound to a visible label. In the hCG labelling zone, the labelling complex will usually comprise an hCG receptor, typically anti-hCG antibody, bound to a visible label. The progesterone labelling complexes are generally comprised of a visible label bound to a progesterone-binding substance (e.g., anti-progesterone antibody) or progesterone receptor. The target hormones in the sample are indirectly labelled and thereby rendered identifiable by specifically binding to the corresponding labelling complex. The capture zone often contains an immobilized second target hormone binding substance, e.g., antibody or hormone or hormone analog.

As explained above, a labelled immunoglobulin that specifically reacts with the target hormone may be the labelling means. The antigen-binding region of a specific immunoglobulin provides for specific binding of the target hormone in the sample. The immunoglobulins may be antibodies of any isotype, such as IgA, IgG, or IgM, Fab fragments, F(ab')$_2$ fragments, Fab' fragments, or the like. The immunoglobulins may be monoclonal or polyclonal and produced by methods as generally described in Harlow and Lane, Antibodies, *A Laboratory Manual*, Cold Spring Harbor Laboratory, 1988, incorporated herein by reference. The labelling complex is not immobilized to the labelling zone so that the fluid sample may solubilize or otherwise remove the labelling complexes into the fluid of the sample.

The receptors may be produced by methods of recombinant DNA technology or isolated from tissue by techniques such as affinity immunopurification as described in Sambrook et al., *Molecular Cloning, A Laboratory Manual*, Cold Spring Harbor Laboratory Press, 2d ed., 1989, incorporated herein by reference.

A variety of visible labels may be bound to the target hormone-binding substances. The labels may be soluble or particulate and may include dyed immunoglobulin binding substances, simple dyes or dye polymers, dyed latex beads, dye-containing liposomes (such as described in U.S. Pat. No. 4,695,554, incorporated herein by reference), dyed cells or organisms, or metallic, organic, inorganic, or dye solids. The labels may be bound to the hormone-binding substance by a variety of means that are well known in the art such as described in U.S. Pat. Nos. 4,863,875 and 4,373,932, each of which is incorporated herein by reference. In some embodiments of the present invention, the labels may be enzymes that can be coupled to a signal producing system, such as described in U.S. Pat. No. 4,366,241, incorporated herein by reference. The same or different labels may be used for each analyte within a single assay device and format.

Because the target hormone labelling complexes contain a target hormone-binding substance and the labelling complexes are solubilized or dispersed into the sample, the target hormone in the sample is contacted and bound by the labelling complexes prior to entering the capture zone. In this manner, target hormones in the sample are indirectly labelled. As labelled target hormones are retained in the capture zone of the device, the labels provide a means for detection of the retained target hormones.

Immobilization of the target hormone-binding substance will generally be accomplished by application of the target hormone binding substance to the capture zone in a suitable buffer, followed by non-specific blocking of surrounding areas with bovine serum albumin, non-fat milk, or the like.

The first target hormone-binding substance and the second target hormone-binding substance will generally bind different regions of the hormone. The second target hormone-binding substance may bind the target hormone-first target hormone binding substance conjugate while not binding unconjugated target hormone. Immunoglobulins that bind target hormone may be monoclonal or polyclonal. Persons of skill in the art are well acquainted with methods of preparing such immunoglobulins, such as described in Harlow and Lane, *Antibodies, A Laboratory Manual*, Cold Spring Harbor Laboratory 1988, incorporated herein by reference. Naturally occurring target hormone receptor may also be employed as a target hormone binding substance in embodiments in which the first target hormone-binding substance is not the target hormone receptor.

The accumulation of label will generally be assessed visually. This visual detection may allow for detection of different colors, e.g., red color or green color, depending upon the target hormone being measured. Accumulated label may also be detected by optical detection devices, such as reflectance analyzers, video image analyzers and the like. The visible intensity of accumulated label could correlate with the concentration of target hormone in the sample. Depending upon the target hormone and the test strip this may be directly or inversely proportional to analyte concentrations. The correlation between the visible intensity of accumulated label and the target hormone concentration may be made by comparison of the visible intensity to a reference standard if desired.

The assay strips may also employ a competitive binding format. These assay strips typically do not contain a labelling zone or labelling complexes. Therefore, target hormone in the sample is generally not labelled. The capture zone contains either immobilized target hormone-binding substance that is bound to labelled target hormone or immobilized target hormone that is bound to labelled target hormone-binding substance. In either case, as unlabelled target hormone in the sample flows into the capture zone, binding between the target hormone and target hormone-binding substance is competitively disrupted, causing displacement of the label from the capture zone. The resulting diminution of signal in the capture zone may then be correlated with the amount of target hormone in the sample. If the labeling complex employs derivatized hormone binding substance it may in the presence of analyte bypass the first capture zone and then be bound in a second anti-ligand binding zone to produce color.

Referring now to FIGS. 1–5, an exemplary test device 10 constructed in accordance with the principles of the present invention is illustrated. The device 10 includes an outer casing 12, typically formed from molded plastic, and an inner flow matrix 14, schematically illustrated in FIG. 5. Casing 12 has a sample application port 16 disposed over sample receiving zone 18 on the flow matrix 14. Labelling region 20 is disposed in the matrix 14 downstream from the sample receiving zone 18. The labelling region 20 includes a first labelling zone 22 having hCG-binding substance bound to visually observable particles disposed therein and a second labelling zone 24 having progesterone or progesterone metabolite-binding substance attached to a visually observable particle immobilized therein. As discussed above, the zones 22 and 24 are shown separately, but could be formed within the same physical region of the labelling region 20.

Capture zone 30 is disposed in the flow matrix 14 downstream from the labelling region 20. Capture zone 30 includes separate, axially-spaced apart capture zones 32 and 34. The first capture zone 32 comprises progesterone, progesterone metabolite, or an analog of progesterone or progesterone metabolite fixed therein. The substance will be attached to the matrix so that it will not be physically displaced by the flow of sample therethrough. In that way, the progesterone or progesterone metabolite, or analog, will be able to competitively bind to the label hCG-binding substance which flows with the sample from the labelling zone 22.

Capture zone 34 comprises an hCG-binding substance fixed therein. The fixed hCG binding substance will be able to capture visible labels which have bound to hCG present in the sample applied to sample receiving zone 18.

An absorbent region 40 is provided to absorb excess sample which has passed through the upstream portions of the matrix to assure that substantially all the sample will pass through each of the labelling and capture zones.

Figure 3:
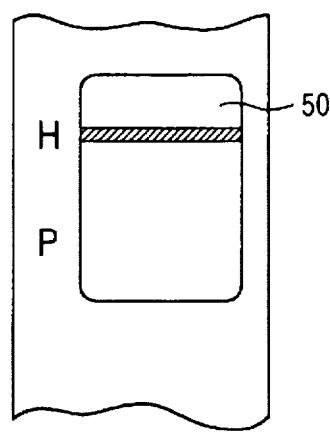
FIG. 3 is a view similar to FIG. 2, shown with label bound within the hCG capture zone.
Figure 4:
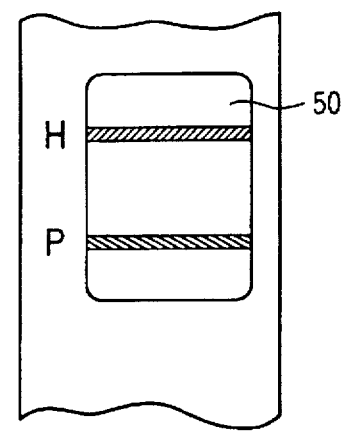
FIG. 4 is a view similar to FIG. 2, shown with label bound within both the hCG captures zone and the progesterone capture zone.
Figure 5:
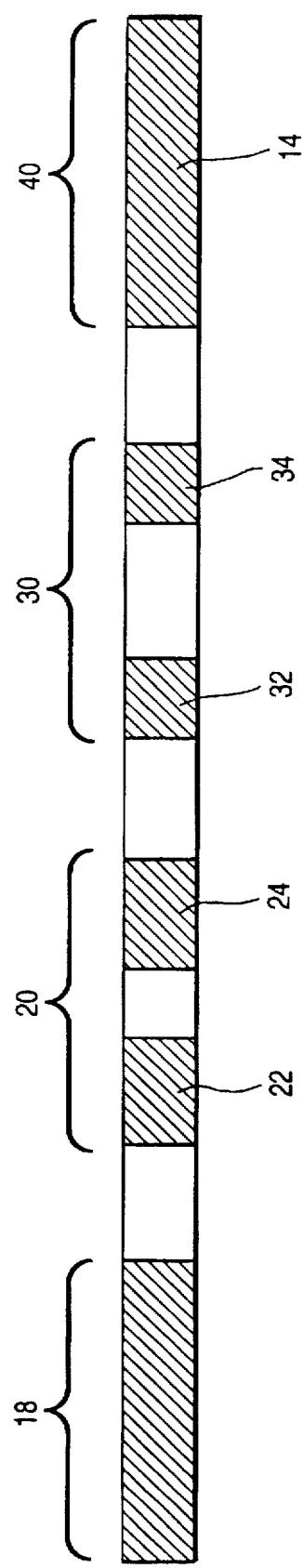
FIG. 5 is a schematic, cross-sectional view of the device of FIG. 1.

The results of the assay are read through an aperture 50 formed in the upper surface of the casing 12. Prior to reaction, no visible marks are apparent through the aperture 50. After being exposed to a patient sample from a female experiencing a normal pregnancy, the presence of the threshold levels of hCG and progesterone or progesterone metabolite will be indicated by the presence of label in the reaction zone 34 and absence of label in zone 32, as illustrated in FIG. 3. Patient sample associated with an abnormal pregnancy having a threshold amount of hCG but below the threshold amount of progesterone or progesterone metabolite results in label bound within both reaction zones 32 and 34, as illustrated in FIG. 4.

EXPERIMENTAL

The following examples are offered by way of illustration, not by way of limitation.

Example 1

Preparation of a one-step assay device for the simultaneous determination of hCG and progesterone in serum.

The following reagents are obtained or prepared. Blue latex beads (0.4 µm diameter) are coated with monoclonal anti-hCG antibody as described in published PCT Application WO92/12428. Polyclonal anti-hCG antibodies are obtained. Dye-complexed horse radish peroxidase (HRP) is conjugated to monoclonal anti-progesterone antibody as described in published PCT Application WO94/01755. Progesterone 3-(O-carboxymethyl)oxime is conjugated to bovine serum albumin (BSA).

The assay device may be prepared using a nitrocellulose membrane by the methods described generally in published PCT Application WO92/12428. The sample receiving zone is prepared as described in said PCT publication. Combined first and second labelling zones are prepared by mixing the blue latex beads coated with anti-hCG antibody and the dye-complexed HRP conjugate of monoclonal anti-progesterone antibody together and applying the mixture to the labelling zone as described in WO92/12428. A first capture zone in the capture region is prepared by applying anti-hCG antibody along a first line. A second capture zone in the capture region is prepared by applying the progesterone 3-(O-carboxymethyl)oxime:BSA along a second line spaced apart from the first line. The nitrocellulose membrane is then blocked according to the procedure described in WO92/12428. The device is then assembled in an outer casing 12 as shown in FIG. 1.

Example 2

Preparation of a one-step assay device for the simultaneous and semi-quantitative determination of hCG and progesterone in serum.

Figure 7:
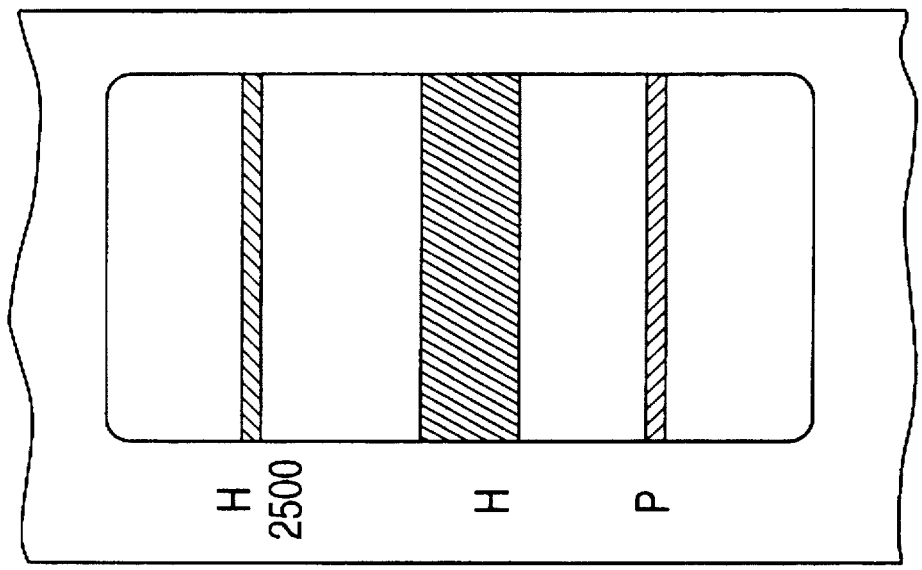
FIG. 7 shows an alternative label zone for a one-step assay device for the simultaneous and semiquantitative determination of hCG and progesterone with one hCG capture line and a single broad hCG capture zone.
Figure 6:
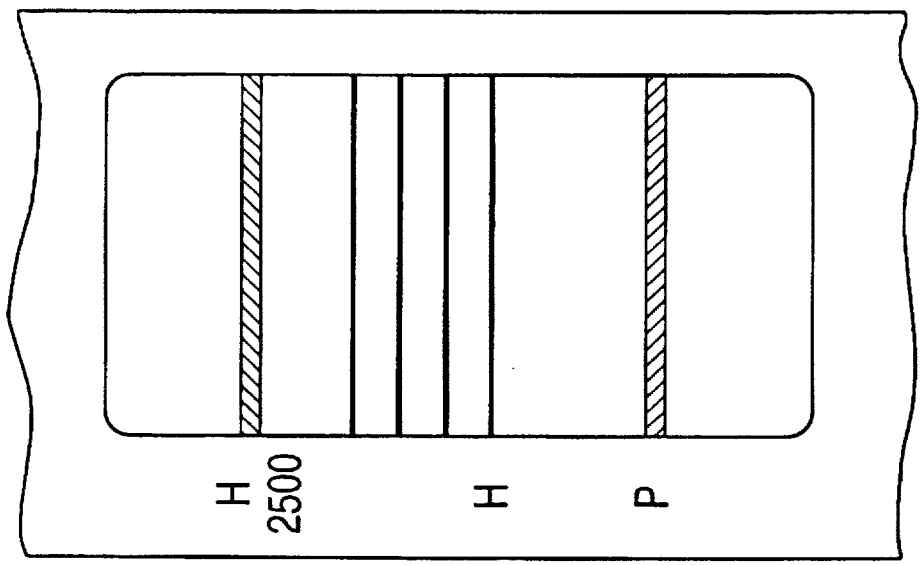
FIG. 6 shows a detailed view of the label zone of a one-step assay device for the simultaneous and semiquantitative determination of hCG and progesterone with multiple hCG capture lines.

A test device is prepared generally as described in Example 1, except that five goat anti-hCG lines are applied in an axially spaced-apart manner, with the final line having a higher antibody concentration than the initial four lines. Antibody concentrations in the lanes were selected to remove varying levels of hCG, i.e. 500, 1000, 1500, 2000, and 2500 mIU, respectively. Such a device is illustrated in FIG. 6. The antibody concentrations are selected so that the final line (shown as H 2500) shows color only when patient hCG concentration exceeds 2500 mIU/ml. The first line (shown aligned with the H) will show color at a threshold concentration of 25 mIU/ml or above. Thus, the device will be able to semi-quantitatively detect serum hCG levels of (i) below 25 mIU/ml, (ii) between 25 and 2500 mIU/ml, and (iii) above 2500 mIU/ml. An alternative structure for semi-quantitative determination hCG is shown in FIG. 7. There, a single wide line for detecting hCG concentration between 25 mU/ml and 2500 mIU/ml is provided. A second line downstream from the first line is provided for indicating hCG concentrations of 2500 mIU/ml or higher. A serial rise in hCG level from day to day may also be used to indicate viable pregnancy when progesterone levels remain above 25 ng/ml. When the hCG level is below 1000 mIU/ml eight weeks after conception, even when the progesterone level is above 25 ng/ml, the pregnancy may be at risk and the patient should be further evaluated.

Example 3

Use of the devices of FIG. 6 for simultaneous and semi-quantitative determination of hCG and progesterone in serum.

A serum sample (120 µl) is applied to the sample receiving zone. Five minutes later, the results are read. The appearance of a red line at the P (progesterone) location indicates a serum progesterone level that is lower than 25 ng/ml. The appearance of a blue band at the first H (hCG) location indicates the presence of a threshold level of hCG above 25 mIU/ml with appearance of color at the H 2500 line indicating that the hCG concentration is greater than 2500 mIU/ml. Serum hCG concentrations above 2500 mIU/ml with progesterone values above 25 ng/ml generally indicate normal pregnancy. Serum hCG concentrations below 2500 mIU/ml with progesterone values above 25 ng/ml, however, can indicate a problem, with the degree to which the value is below 2500 mIU/ml generally correlating with the seriousness of the problem.

A chart which sets forth the interpretation of both semi-quantitative and threshold detection progesterone-hCG assays is provided below.

| Serum Progesterone Level (ng/ml) | Serum hCG Level (mIU/ml) | Interpretation* |
|---|---|---|
| <25 | <25 | SAB |
| <25 | >25–<2500 | SAB, EP |
| <25 | >2500 | IUP at risk, HM/T |
| >25 | <25 | Recently aborted |
| >25 | >25–<2500 | IUP at risk |
| >25 | >2500 | Normal IUP |
| >25 | Rising** | Normal IUP likely |
| >25 | 2500 | Normal IUP |
| <25 | Not rising | IUP at risk |
| <25 | Elevated | HM/T |
| >25 | >2500 | Normal IUP |
| >25 | <2500 | Abnormal IUP |
| <25 | >2500 | Normal IUP, HM/T |
| <25 | <2500 | IUP at risk |

*SAB = Spontaneous abortion
EP = Ectopic pregnancy
IUP = Intrauterine pregnancy
HM/T = Hydatidiform mole or tumor
**Two-fold daily increases in hCG level Although the foregoing invention has been described in some detail by way of illustration and example, for purposes of clarity of understanding, it will be obvious that certain changes and modifications may be practiced within the scope of the appended claims.

What is claimed is:

1. A one step method for assisting in distinguishing between normal and abnormal pregnancies in human females, said method comprising:

directly applying a specimen from the female to a lateral flow matrix, wherein the specimen is selected from the group consisting of blood, plasma, serum, and urine;

selectively binding or depleting a visually observable label within a first binding region on the flow matrix, wherein binding or depletion occurs when the concentration of progesterone in the specimen falls below a threshold value in the range from 5 ng/ml to 50 ng/ml in blood, plasma, or serum, or when the concentration of a progesterone metabolite falls below a corresponding value in urine; and selectively binding or depleting a visually observable label within a second binding region on the flow matrix, wherein binding or depleting occurs when the human chorionic gonadotropin (hCG) concentration exceeds a threshold value in the range from 25 mIU/ml to 100 mIU/ml in the specimen;

wherein absence of label in the first binding region and the presence of label in the second binding region are indicative of a normal pregnancy, presence of label in the first and second binding regions is indicative of an abnormal pregnancy, and absence of label in the second binding region is indicative that the method is not functioning properly or that the female is not pregnant.

2. A method as in claim 1, wherein the selective binding steps comprise binding a colored particle within the binding regions.

3. A test device for distinguishing between normal and abnormal pregnancies in human females, said device comprising:

a lateral flow matrix defining a flow path for receiving a patient sample;

first means on the matrix for indicating when a progesterone or progesterone metabolite concentration in the sample exceeds a threshold value, wherein the first means provides a visual label when the progesterone or progesterone metabolite concentration is below the threshold value; and second means on the matrix for indicating when human chorionic gonadotropin (hCG) concentration in the sample exceeds a threshold value, wherein the second means provides a visual label when the hCG concentration exceeds the threshold value;

wherein absence of label in the first means and presence of label in the second means are indicative of a normal pregnancy, presence of label in the first and second means is indicative of an abnormal pregnancy, and absence of label in the second means is indicative that the device is functioning improperly or that the female is not pregnant.

4. A test device as in claim 3, wherein absence of visual label in the first means indicates a progesterone concentration above a threshold value in the range from 5 ng/ml to 50 ng/ml or a corresponding progesterone metabolite concentration.

5. A test device as in claim 4, wherein the corresponding progesterone metabolite concentration is a progesterone-3α-glucuronide (PDG) concentration in the range from 5 µg/ml to 50 µg/ml.

6. A test device as in claim 3, wherein presence of visual label in the second means indicates a hCG concentration above a threshold value in the range from 25 mIU/ml to 100 mIU/ml.

7. A test device as in claim 3, wherein the first means comprises:
- a sample-receiving zone at an upstream end of the flow path;
- a labeling zone on the flow path downstream from the sample-receiving zone, said labeling zone having means for attaching visual label to progesterone or progesterone metabolite in sample flowing through said labeling zone; and
- a capture zone on the flow path downstream from the labeling zone, said capture zone having means for capturing visual label which has not bound to progesterone or progesterone metabolite in the labeling zone, wherein presence of label in the capture zone is indicative of a progesterone or progesterone metabolite concentration below the threshold value.

8. A test device as in claim 3, wherein the second means comprises:
- a sample-receiving zone at an upstream end of the flow path;
- a labeling zone on the flow path downstream from the sample-receiving zone, said labeling zone having means for attaching visual label to hCG in sample flowing through said labeling zone; and
- a capture zone on the flow path downstream from the labeling zone, said capture zone having means for capturing visual label which has been bound to hCG, wherein presence of label in the capture zone is indicative of an hCG concentration above the threshold value.

9. A test device for distinguishing between normal and abnormal pregnancies in human females, said device comprising:
- a lateral flow matrix defining a flow path from an upstream end to a downstream end;
- a sample-receiving zone disposed on the flow path near its upstream end;
- a first labeling zone disposed on the flow path downstream from the sample-receiving zone, said first labeling zone comprising a hCG-binding substance bound to a visually observable particle, wherein hCG present in sample flowing through the first labeling zone will bind to the observable particle;
- a second labeling zone disposed on the flow path downstream from the sample-receiving zone, said second labeling zone comprising a progesterone- or progesterone metabolite-binding substance attached to a visually observable particle, wherein progesterone or progesterone metabolite present in the sample flowing through the second labeling zone will bind to the observable particle;
- a first capture zone disposed on the flow path downstream from the first labeling zone, said first capture zone comprising an hCG-binding substance so that visually observable particles having hCG bound thereto will bind within the first capture zone when the hCG concentration in the sample exceeds a threshold value; and
- a second capture zone disposed on the flow path downstream from the second labeling zone, said second capture zone comprising progesterone, a progesterone metabolite, or an analog of progesterone or a progesterone metabolite, so that visually observable particles having a progesterone- or progesterone metabolite-binding substance bound thereto will bind within the second capture zone when the progesterone or progesterone metabolite concentration in the sample falls below a threshold value;

wherein presence of visual label in the first capture zone and absence of visual label in the second capture zone are indicative of a normal pregnancy, presence of visual label in the first and second capture zones is indicative of an abnormal pregnancy, and absence of visual label in the first capture zone indicates that the device is functioning improperly or the female is not pregnant.

10. A test device as in claim 9, wherein the amount of hCG-binding substance in the first labeling zone is in excess over the amount needed to bind the threshold value of hCG and wherein the amount of hCG-binding substance in the capture zone is in excess over the amount needed to bind the threshold value of hCG, whereby binding of label within the capture zone is directly proportional to the amount of hCG in the sample.

11. A test device as in claim 10, wherein the threshold value is in the range from 25 mIU/ml to 100 mIU/ml.

12. A test device as in claim 9, wherein the amount of progesterone- or progesterone metabolite-binding substance present in the labelling zone is limited, so that an amount of progesterone or progesterone metabolite in the sample above the threshold value will bind substantially all labelled binding substance so that binding of said labelled binding substance within the capture zone is prevented.

13. A test device as in claim 12, wherein the threshold value is in the range of 5 ng/ml to 50 ng/ml for progesterone and 5 µg/ml to 50 µg/ml for PDG.

14. A method as in claim 1, wherein the test is performed during the first six months of pregnancy.

15. A method as in claim 14, wherein the test is performed from 4 weeks to 3 months after conception.

16. A test device as in claim 3, said device further comprising:
- third means on the matrix for indicating when human chorionic gonadotropin (hCG) concentration in the sample exceeds a second hCG threshold value.

17. The test device of claim 16, wherein the hCG threshold value is in the range from 25 mIU/ml to 100 mIU/ml and the second hCG threshold value is about 2500 mIU/ml.

18. A combination of a first and a second test device, wherein the first device comprises:
- a lateral flow matrix for receiving a patient sample; and
- a first means on the matrix for indicating when a progesterone concentration in the sample exceeds a threshold value in the range from 5 ng/ml to 50 ng/ml or a corresponding progesterone metabolite concentration exceeds a corresponding threshold value, wherein the first means provides a visual label when the progesterone or progesterone metabolite concentration is below the threshold value;

wherein the second device comprises:
- a second lateral flow matrix for receiving a patient sample; and
- a second means on the matrix for indicating when human chorionic gonadotropin (hCG) concentration in the sample exceeds a threshold value in the range from 25 mIU/ml to 100 mIU/ml, wherein the second means provides a visual label when the hCG concentration exceeds the threshold value;

wherein absence of visual label in the first means and presence of visual label in the second means are indicative of a normal pregnancy, presence of visual label in the first and second means is indicative of an abnormal pregnancy, and absence of visual label in the second means indicates that the second test device is not functioning properly or that the female is not pregnant.

19. A test device for distinguishing between normal and abnormal pregnancies in human females, said device comprising:

a lateral flow matrix defining a flow path from an upstream end to a downstream end;

a sample-receiving zone disposed on the flow path near its upstream end;

a first labeling zone disposed on the flow path downstream from the sample-receiving zone, said first labeling zone comprising a hCG-binding substance bound to a visually observable particle, wherein hCG present in sample flowing through the first labeling zone will bind to the observable particle;

a second labeling zone disposed on the flow path downstream from the sample-receiving zone, said second labeling zone comprising a progesterone, a progesterone metabolite, or an analog of progesterone or progesterone metabolite, bound to a visually observable particle;

a first capture zone disposed on the flow path downstream from the first labeling zone, said first capture zone comprising an hCG-binding substance so that visually observable particles having hCG bound thereto will bind within the first capture zone when the hCG concentration in the sample exceeds a threshold value; and a second capture zone disposed on the flow path downstream from the second labeling zone, said second capture zone comprising progesterone- or a progesterone metabolite-binding substance, so that visually observable particles having a progesterone or progesterone metabolite bound thereto will bind within the second capture zone when the progesterone or progesterone metabolite concentration in the sample falls below a threshold value;

wherein presence of visual label in the first capture zone and absence of visual label in the second capture zone are indicative of a normal pregnancy, presence of visual label in the first and second capture zones is indicative of an abnormal pregnancy, and absence of visual label in the first capture zone indicates that the device is functioning improperly or the female is not pregnant.

* * * * *